United States Patent [19]

Ogura

[11] Patent Number: 5,727,560
[45] Date of Patent: *Mar. 17, 1998

[54] BLOOD PRESSURE MEASURING APPARATUS

[75] Inventor: Toshihiko Ogura, Inuyama, Japan

[73] Assignee: Colin Corporation, Komaki, Japan

[*] Notice: The term of this patent shall not extend beyond the expiration date of Pat. No. 5,680,869.

[21] Appl. No.: 714,850

[22] Filed: Sep. 17, 1996

[30] Foreign Application Priority Data

Sep. 20, 1995 [JP] Japan .................................. 7-241093

[51] Int. Cl.$^6$ ........................................................ A61B 5/06
[52] U.S. Cl. .................................................. 128/681; 128/682
[58] Field of Search ..................................... 128/672, 677, 128/680–687

[56] References Cited

U.S. PATENT DOCUMENTS

| | | |
|---|---|---|
| 4,228,506 | 10/1980 | Ripley et al. . |
| 4,747,412 | 5/1988 | Yamaguchi .......................... 128/682 |
| 4,944,305 | 7/1990 | Takatsu et al. ........................ 128/683 |
| 4,967,756 | 11/1990 | Hewitt .................................. 128/680 |
| 4,995,399 | 2/1991 | Hayashi et al. ....................... 128/680 |
| 5,337,750 | 8/1994 | Walloch ................................. 128/681 |

FOREIGN PATENT DOCUMENTS

| | | |
|---|---|---|
| 0-208-619 | 1/1987 | European Pat. Off. . |
| 2-6-679-675 | 1/1993 | France . |

*Primary Examiner*—Robert L. Nasser
*Attorney, Agent, or Firm*—Oliff & Berridge, PLC

[57] ABSTRACT

An apparatus for measuring a blood pressure (BP) value of a living subject, including a BP measuring device which measures, in each of measuring operations, at least one BP value of the subject including a systolic BP value of the subject, a first storing device which stores a set of temporary BP data which represents, as at least one temporary BP value, at least one BP value measured by the BP measuring device in each of a plurality of measuring operations within a predetermined time duration, thereby storing a plurality of sets of temporary BP data corresponding to the plurality of measuring operations within the time duration, and a second storing device which selects one of the sets of temporary BP data such that the selected one set of temporary BP data represents at least one temporary BP value including a lowest temporary systolic BP value of the respective temporary systolic BP values represented by the sets of temporary BP data, and stores the selected one set of temporary BP data as a set of proper BP data representing at least one proper BP value obtained within the time duration, the at least one proper BP value including the lowest temporary systolic BP value as a proper systolic BP value.

18 Claims, 6 Drawing Sheets

FIG. 6

BLOOD PRESSURE MEASURING APPARATUS

BACKGROUND OF THE INVENTION

1. Field of the Invention

The present invention relates to a blood pressure measuring apparatus which accumulatively stores measured blood pressure values.

2. Discussion of Related Art

There is known an automatic blood pressure (BP) measuring apparatus including a memory device, such as a magnetic disk. The BP measuring apparatus automatically carries out BP measurements on a living person, and accumulatively stores, in the memory device, measured BP values and other related data. The BP measuring apparatus provides personal health information including the BP values, in the form of a graphic representation of a time-wise trend of the BP values, thereby making it possible for the person to recognize a time-wise change of the BP values. If the person compares the current BP value with the prior BP values stored in the memory device, then he or she can judge whether the manner in which the current BP value is obtained is appropriate and/or whether his or her physical condition is normal.

In the above BP measuring apparatus wherein measured BP values are accumulatively stored, all measured BP values are stored in the memory device even in the case where another or more BP measurements are carried out just for obtaining a more accurate BP value or values than the first BP value or values obtained in the first BP measurement. Thus, the limited memory capacity of the memory device is unnecessarily used. In addition, it is considerably difficult to read an accurate time-wise change of BP values from the graphic representation which contains the inaccurate or unnecessary BP values.

SUMMARY OF THE INVENTION

It is therefore an object of the invention to provide a blood pressure measuring apparatus which does not store unnecessary BP values.

The above object may be achieved according to the present invention, which provides an apparatus for measuring a blood pressure value of a living subject, comprising a blood pressure measuring device which measures, in each of a plurality of measuring operations, at least one blood pressure value of the subject including a systolic blood pressure value of the subject, a first storing device which stores a set of temporary blood pressure data which represents, as at least one temporary blood pressure value, at least one blood pressure value measured by the blood pressure measuring device in each of a plurality of measuring operations within a predetermined time duration, thereby storing a plurality of sets of temporary blood pressure data corresponding to the plurality of measuring operations within the time duration, and a second storing device which selects one of the sets of temporary blood pressure data such that the selected one set of temporary blood pressure data represents at least one temporary blood pressure value including a lowest temporary systolic blood pressure value of the respective temporary systolic blood pressure values represented by the sets of temporary blood pressure data, and stores the selected one set of temporary blood pressure data as a set of proper blood pressure data representing at least one proper blood pressure value obtained within the time duration, the at least one proper blood pressure value including the lowest temporary systolic blood pressure value as a proper systolic blood pressure value.

In the BP measuring apparatus constructed as described above, when two or more BP measurements are carried out for obtaining a more accurate BP value or values than the BP value or values obtained in the first BP measurement or the first and subsequent BP measurements, only the BP value or values obtained in the more or most appropriate measurement is/are stored, which leads to efficient use of a limited memory capacity thereof. In addition, in the case where the present apparatus provides a graphic representation showing a time-wise trend of the stored BP values, the graphic representation does not contain unnecessary BP values, so that the living subject can read a more accurate time-wise change of the BP values from the graphic representation.

According to a preferred feature of the present invention, the BP measuring apparatus further comprises a timer which measures the predetermined time duration.

According to another feature of the present invention, the BP measuring apparatus further comprises a card reader which reads identification data recorded on a data card which is inserted in the card reader by the subject, and the timer starts to measure the predetermined time duration when the blood pressure measuring device starts an initial blood pressure measurement after the card reader reads the identification data from the data card.

According to another feature of the present invention, the BP measuring apparatus further comprises a card reader which reads identification data recorded on a data card which is inserted in the card reader by the subject.

According to another feature of the present invention, the second storing device comprises means for storing the set of proper blood pressure data on the data card being inserted in the card reader.

According to another feature of the present invention, the BP measuring apparatus further comprises a registering device which registers identification data identical with the identification data recorded on the data card, and judging means for judging whether the identification data read by the card reader from the data card inserted by the subject are identical with the identification data registered by the registering device.

According to another feature of the present invention, the second storing device comprises means for accumulatively storing a plurality of the sets of proper blood pressure data in association with the registered identification data.

According to another feature of the present invention, the blood pressure measuring device comprises means for measuring, in the each measuring operation, at least the systolic blood pressure value and a diastolic blood pressure value of the subject.

According to another feature of the present invention, the BP measuring apparatus further comprises a judging means for judging whether the first storing device has stored a single set of temporary blood pressure data, wherein the second storing device comprises means for storing, when the judging means makes a positive judgment, the single set of temporary blood pressure data as the set of proper blood pressure data.

According to another feature of the present invention, the BP measuring apparatus further comprises a output device which outputs a graphic representation indicating a time-wise change of the sets of proper blood pressure data accumulatively stored by the second storing device.

According to another feature of the present invention, the blood pressure measuring device comprises an inflatable cuff which is adapted to be wound around a body portion of the subject.

According to another feature of the present invention, the second storing device comprises means for accumulatively storing a plurality of the sets of proper blood pressure data.

According to another feature of the present invention, the BP measuring apparatus further comprises means for selecting, from the sets of proper blood pressure data stored by the second storing device, an oldest set of proper blood pressure data which is stored by the second storing device prior to any other set of proper blood pressure data.

According to another feature of the present invention, the BP measuring apparatus further comprises means for selecting, from the sets of proper blood pressure data stored by the second storing device, a second latest set of proper blood pressure data which is stored by the second storing device prior to the last stored set of proper blood pressure data.

According to another feature of the present invention, the BP measuring apparatus further comprises means for selecting, from the sets of proper blood pressure data stored by the second storing device, a set of proper blood pressure data representing at least one proper blood pressure value including a highest systolic blood pressure value of the respective proper systolic blood pressure values represented by the sets of proper blood pressure data.

According to another feature of the present invention, the BP measuring apparatus further comprises means for selecting, from the sets of proper blood pressure data stored by the second storing device, a set of proper blood pressure data representing at least one proper blood pressure value including a lowest systolic blood pressure value of the respective proper systolic blood pressure values represented by the sets of proper blood pressure data.

According to another feature of the present invention, the second storing device comprises means for storing the set of proper blood pressure data together with data representing a time when the set of proper blood pressure data is obtained.

According to another feature of the present invention, the BP measuring apparatus further comprises a pulse-rate measuring device which measures a pulse-rate value of the subject, and wherein the second storing device stores the set of proper blood pressure data together with data representing the pulse-rate value measured when the proper blood pressure value represented by the set of proper blood pressure data is measured by the blood pressure measuring device.

BRIEF DESCRIPTION OF THE DRAWINGS

The above and optional objects, features, and advantages of the present invention will better be understood by reading the following detailed description of the preferred embodiments of the invention when considered in connection with the accompanying drawings, in which.

DETAILED DESCRIPTION OF THE PREFERRED EMBODIMENTS

Referring to FIGS. 1 to 6, there will described an automatic blood pressure (BP) measuring apparatus 10 to which the present invention is applied.

Figure 1:
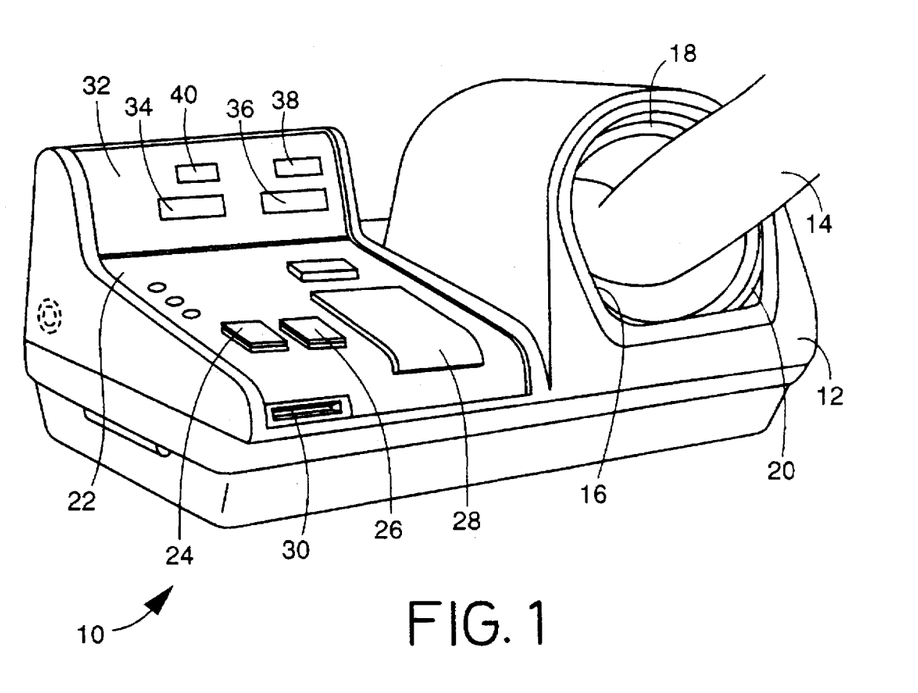
FIG. 1 is a perspective view of a blood pressure (BP) measuring apparatus as one embodiment of the present invention.

In FIG. 1, reference numeral 12 designates a housing of the BP measuring apparatus 10. The BP measuring apparatus 10 includes a tunnel-like, cylindrical hollow portion which provides an arm receiver 16 into which an arm 14 of a living subject is inserted for measurement of his or her BP value. Inside the arm receiver 16, an elongate belt 20 is supported such that the belt 20 takes a generally cylindrical shape. An inflatable cuff 18 which is provided by a flexible cloth bag and a rubber bag accommodated in the cloth bag, is secured to the inner surface of the elongate belt 20.

The BP measuring apparatus 10 has an operation panel 22 including a START switch 24, a STOP switch 26, a printer 28, and a card insertion slot 30. The BP measuring apparatus 10 further has a display panel 32 including a SAP display 34, a DAP display 36, a PR display 38, and a date and time display 40. The abbreviations "SAP", "DAP", and "PR" represent a systolic BP value, a diastolic BP value, and a pulse rate, respectively.

Figure 2:
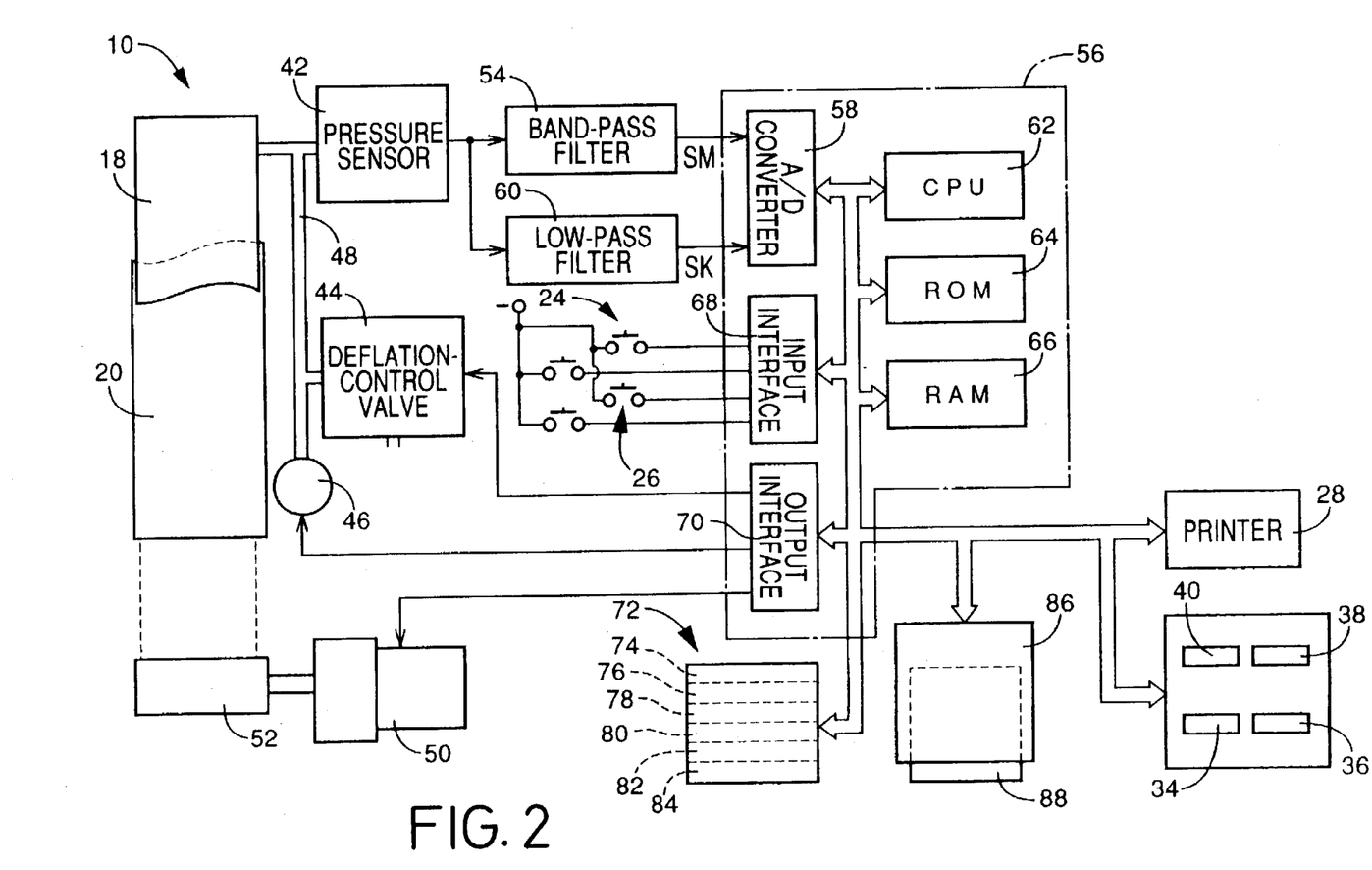
FIG. 2 is a block diagram showing the construction of the apparatus of FIG. 1.

FIG. 2 shows the construction of the BP measuring apparatus 10. In the figure, the inflatable cuff 18 is connected via piping 48 to a pressure sensor 42, a deflation-control valve 44, and an air pump 46. The pressure sensor 42 detects an air pressure in the cuff 18 and outputs an electric signal representing the detected cuff pressure. The elongate belt 20 which takes a cylindrical shape in the arm receiver 16 and to which the inflatable cuff 18 is secured, is fixed at one of longitudinal ends thereof to the housing 12 and is connected at the other longitudinal end to a rotatable drum 52 which is driven or rotated by a direct-current (DC) motor 50 via reduction gears. The elongate belt 20 or the inflatable cuff 18 is tightened, and loosened, by the DC motor 50.

The output signal of the pressure sensor 42 is supplied to a band-pass filter 54, which extracts, from the received signal, an alternating-current (AC) component representing a pulse wave, i.e., pressure oscillation propagated from the subject to the cuff 18 and supplies the extracted AC component as a pulse-wave signal, SM, to an analog to digital (A/D) converter 58 of an electronic control circuit 56. The pulse wave represented by the pulse-wave signal SM is produced from the brachial artery of subject's arm 14 being pressed under the cuff 18, and is propagated to the cuff 18. The output signal of the pressure sensor 42 is also supplied to a low-pass filter 60, which extracts, from the received signal, a direct-current (DC) component representing a static pressure in the cuff 18 and supplies the extracted DC component as a cuff-pressure signal, SK, to the A/D converter 58 of the control circuit 56. The static cuff pressure represented by the cuff-pressure signal SK changes when the cuff 18 is tightened or loosened by the DC motor 50.

The electronic control circuit 56 is provided by a microcomputer including a central processing unit (CPU) 62, a read only memory (ROM) 64, a random access memory (RAM) 66, an input interface circuit 68, and an output interface circuit 70. The CPU 62 processes input signals according to the control programs pre-stored in the ROM 64 by utilizing the temporary-storage function of the RAM 66, outputs a drive signal to the printer 28, and outputs display signals to the displays 34-40. When a BP measurement is carried out, the CPU 62 supplies a drive signal to the DC motor 50 to wind the cuff 18 around the upper arm 14 of the subject being inserted in the arm receiver 16, subsequently supplies a drive signal to the air pump 46 to inflate the cuff 18 and thereby press the upper arm 14, and then supplies a drive signal to the deflation-control valve 44 to reduce gradually or slowly the pressure of the cuff 18, so that the CPU 62 obtains the pulse-wave signal SM and the cuff-pressure signal SK from the pressure sensor 42 via the respective filters 54, 60 during this cuff-pressure reducing operation, determines a systolic and a diastolic BP values SAP, DAP of the subject in a known oscillometric BP measuring method based on the obtained signals SM, SK, and supplies display signals to the SAP and DAP displays 34, 36 to display the determined BP values SAP, DAP, respectively.

In addition, the CPU 62 produces a set of temporary BP data which represents the thus determined BP values SAP, DAP as temporary BP values, and represents a date and a time when the BP values are obtained, and stores the set of temporary BP data in a temporary BP data memory area 74 of a BP-data storing device 72. The CPU 62 accumulatively stores a plurality of sets of temporary BP data produced in a plurality of BP measurements carried out within five minutes after the first one of BP measurements is started on the BP measuring apparatus 10. The CPU 62 selects, from all the sets of temporary BP data accumulatively stored in the temporary BP data memory area 74 within the five minutes, one set of temporary BP data which represents the lowest systolic BP value SAP of the respective systolic BP values SAP represented by all the stored sets of temporary BP data, and stores the selected set of temporary BP data, as a set of proper BP data representing proper systolic and diastolic BP values, in a proper BP data memory area 76 of the BP-data storing device 72.

Furthermore, the CPU 62 selects, from all the sets of proper BP data accumulatively stored in the proper BP data memory area 76, one set of proper BP data representing the oldest date and time, and stores the selected set of proper BP data in an early BP data memory area 78 of the BP-data storing device 78; the CPU 62 selects, from all the sets of proper BP data stored in the proper BP data memory area 76, one set of proper BP data representing the second latest date and time, and stores the selected set of proper BP data in a late BP data memory area 80 of the storing device 72; the CPU 62 selects, from all the sets of proper BP data stored in the proper BP data memory area 76, one set of proper BP data representing the highest systolic BP value SAP of the respective systolic BP values SAP represented by all the stored sets of proper BP data (except the two sets of proper BP data stored in the early and late BP data memory areas 78, 80, respectively), and stores the selected set of proper BP data in a highest-SAP BP data memory area 82 of the storing device 72; and the CPU 62 selects, from all the sets of proper BP data stored in the proper BP data memory area 76, one set of proper BP data representing the lowest systolic BP value SAP of the respective systolic BP values SAP represented by all the stored sets of proper BP data (except the two sets of proper BP data stored in the early and late BP data memory areas 78, 80, respectively), and stores the selected set of proper BP data in a lowest-SAP BP data memory area 84 of the storing device 72. The BP-data storing device 72 is provided by a well-known memory device such as a magnetic disk, a magnetic tape, a volatile semiconductor memory, or a non-volatile semiconductor memory.

Hereinafter, there will be described the operation of the automatic BP measuring apparatus 10 constructed as described above, by reference to the flow charts of FIGS. 3, 4, and 5.

Figure 3:
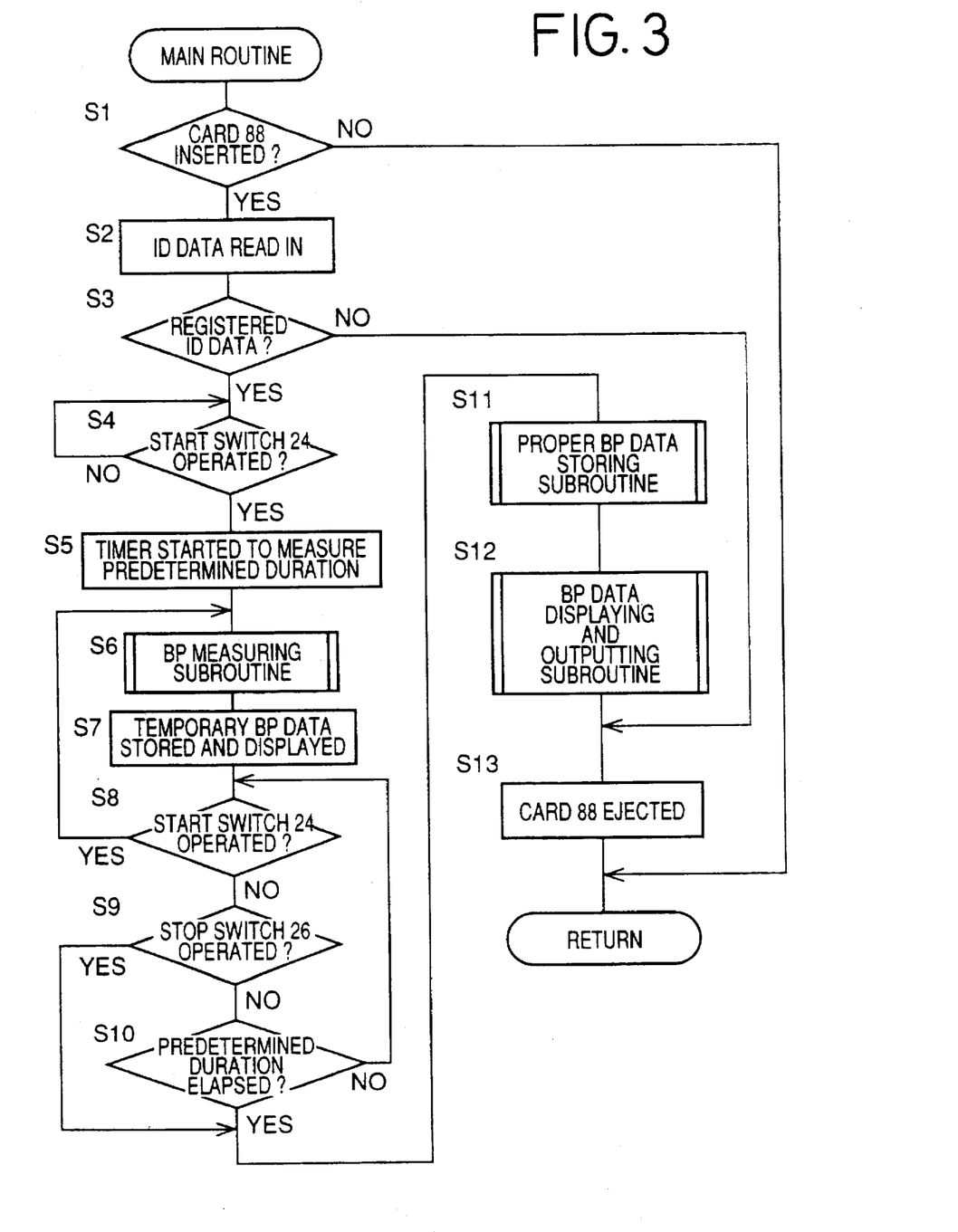
FIG. 3 is a flow chart representing a control program according to which the apparatus of FIG. 1 is operated.

First, at Step S1 of FIG. 3, the CPU 62 judges whether a magnetic card 88 has been inserted in a card reader 86 through the insertion slot 30 by a living person. If a negative judgment is made at Step S1, the current cycle of the main routine is ended. On the other hand, if a positive judgment is made at Step S1, the control of the CPU 62 goes to Step S2 to read identification (ID) data which are magnetically recorded on the magnetic card 88 and which identify the person who carries the card 88.

Step S2 is followed by Step S3 to judge whether the ID data read from the magnetic card 88 are identical with ID data registered in an appropriate memory area of the BP-data storing device 72. If a negative judgment is made at Step S3, the control of the CPU 62 goes to Step S13 to eject the magnetic card 88 from the card reader 86 through the slot 30. On the other hand, if a positive judgment is made at Step S3, i.e., the ID data read from the magnetic card 88 are identical with registered ID data, the control of the CPU 62 goes to Step S4 to judge whether the START switch 24 has been operated to start a blood pressure (BP) measurement.

If the judgment made at Step S4 is negative, Step S4 is repeated until a positive judgment is made. Meanwhile, if a positive judgment is made at Step S4, the control of the CPU 62 goes to Step S5 to start a timer to measure a predetermined time duration, i.e., 5 minutes during which a plurality of BP measurements may be carried out on the person. Step S5 is followed by Step S6 to effect a BP measuring subroutine in which a systolic, a diastolic, and a mean BP value SAP, DAP, MAP, and a pulse-rate value PR, of the person are measured. This measurement is the first measurement within the five minutes after the timer is started at Step S5. More specifically described, the pressure of the cuff 18 is automatically increased according to a predetermined procedure, and the BP values SAP, DAP, MAP of the person are determined based on the signals SM, SK obtained during the slow decreasing of the cuff pressure, in the known oscillometric BP measuring method. The systolic and diastolic BP values SAP, DAP are determined based on the variation of respective magnitudes of heartbeat-synchronous pulses of the pulse-wave signal SM obtained during the slow cuff-pressure decreasing. The mean BP value MAP is determined as being equal to the cuff pressure at the time of occurrence or detection of a heartbeat-synchronous pulse having the greatest or maximum amplitude. The pulse-rate value PR is determined from the time interval between the respective times of detection of two successive heartbeat-synchronous pulses of the pulse-wave signal SM which is the same as used to determine the BP values SAP, DAP, MAP.

Step S6 is followed by Step S7 to store a set of temporary BP-PR data which represents the BP and pulse-rate values SAP, DAP, MAP, PR determined at Step S6, as temporary BP and pulse rate values, and represents the date and time of measurement of those values, in the temporary BP data memory area 74 of the BP-data storing device 72. Further, at Step S7, the determined BP and pulse-rate values SAP, DAP, PR are displayed on the SAP, DAP, and PR displays 34, 36, 38, respectively.

Step S7 is followed by Step S8 to judge whether the START switch 24 has been operated again to start another BP measurement. If a positive judgment is made at Step S8, Steps S6 and S7 are repeated. In this case, data indicative of the values SAP, DAP, MAP, PR obtained at Step S6 in the second measurement are stored, as another set of temporary BP data, in the temporary BP data memory area 74 of the BP-data storing device 72. On the other hand, if a negative judgment is made at Step S8, that is, if the START switch 24 has not been operated, the control of the CPU 62 goes to Step S9 to judge whether the STOP switch 26 has been operated not to carry out any more BP measurement. If a positive judgment is made at Step S9, no additional measurement is carried out. Accordingly, even if the predetermined time duration (i.e., 5 minutes) may not have elapsed yet, the control of the CPU 62 goes to Step S11. On the other hand, if a negative judgment is made at Step S9, the control goes to Step S10 to judge whether the timer which had been started at Step S5 has measured the predetermined time duration, i.e., 5 minutes. If a negative judgment is made at Step S9, it means that another BP measurement may be ordered by the person. In this case, Step S8 and the following steps are repeatedly executed. Meanwhile, if a positive judgment is made at Step S10, namely, if the timer has measured the 5 minutes, Step S10 is followed by Step S11 to effect a proper BP data storing subroutine.

Figure 4:
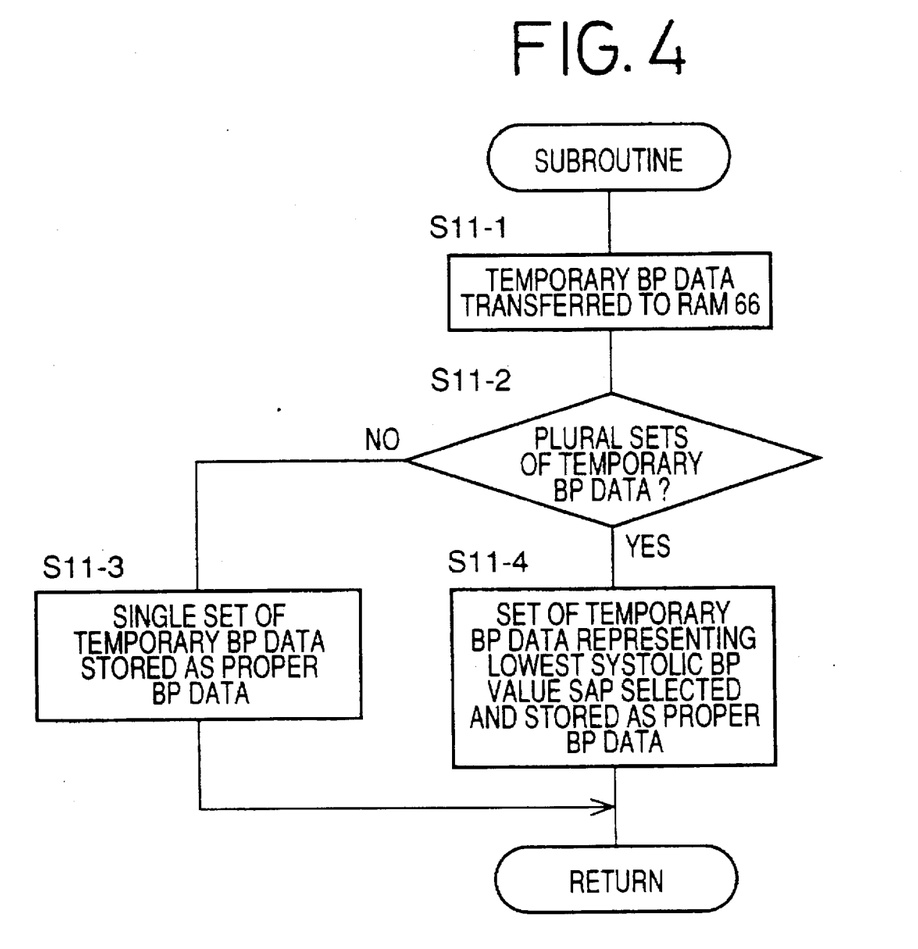
FIG. 4 is a flow chart representing a subroutine effected at Step S11 of the flow chart of FIG. 3.

The proper BP data storing subroutine of Step S11 is represented by the flow chart of FIG. 4. This subroutine starts with Step S11-1 to transfer the set or sets of temporary BP data stored in the temporary BP data memory area 74 of the BP-data storing device 72, to the RAM 66. Step S11-1 is followed by Step S11-2 to judge whether a plurality of BP measurements have been effected within the predetermined time, namely, a plurality of sets of temporary BP data have been stored in the temporary BP data memory area 74 as a result of execution of a plurality of cycles of the BP measuring subroutine of Step S6. If a negative judgment is made at Step S11-2, it means that only one BP measurement has been effected, and the control of the CPU 62 goes to Step S11-3 to store the single set of temporary BP data as a set of proper BP data, in the proper BP data memory area 76. That is, data indicative of the measured values SAP, DAP, MAP, PR are stored in the proper BP data memory area 76, together with data indicative of the date and time of measurement of those values. On the other hand, if a positive judgment is made at Step S11-2, it means that a plurality of BP measurements have been effected, and the control of the CPU 62 goes to step S11-4 to select the most appropriate set of temporary BP data from the stored sets of temporary BP data, and store the selected set of temporary BP data as a set of proper BP data in the proper BP data memory area 76. More specifically described, at Step S11-4, one of the stored sets of temporary BP data which represents the lowest systolic BP value SAP is stored as the set of proper BP data in the proper BP data memory area 76. The set of proper BP data which represents the values SAP, DAP, MAP, PR as proper values are stored in the proper BP data memory area 76, together with data indicative of the date and time when the predetermined time (i.e., five minutes) has elapsed. At each of Steps S11-3 and S11-4, the set of proper BP data is stored in association with the registered ID data identifying the person.

Figure 5:
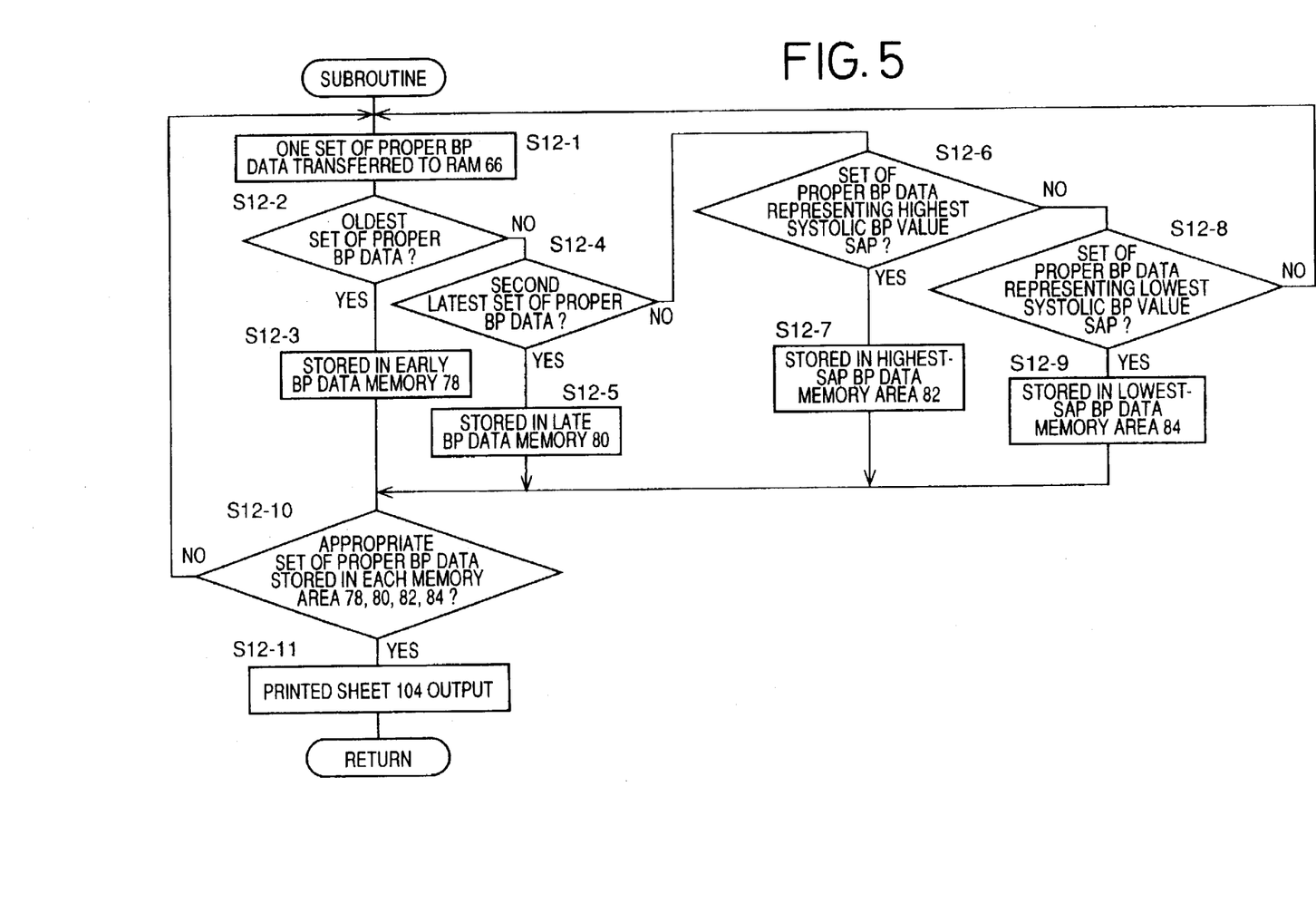
FIG. 5 is a flow chart representing a subroutine effected at Step S12 of the flow chart of FIG. 3.

The proper BP data storing subroutine of Step S11 is followed by Step S12 to effect a displaying and outputting subroutine represented by the flow chart of FIG. 5. The subroutine of FIG. 5 starts with Step S12-1 to transfer, to the RAM 66, each one of the set or sets of proper BP data which have accumulatively been stored in the proper BP data memory area 76 in association with the ID data of the person, in the order of storing of the sets of proper BP data in the proper BP data memory area 76. Subsequently, the control of the CPU 62 goes to Step S12-2 to judge whether the one set of proper BP data transferred to the RAM 66 at Step S12-1 represents the oldest date and time. If the judgment at Step S12-2 is positive, Step S12-2 is followed by Step S12-3 to store the set of proper BP data indicative of the values SAP, DAP, MAP, PR, in the early BP data memory area 78, together with the data indicative of the date and time of measurement of those values.

If a negative judgment is made at Step S12-2, the control of the CPU 62 goes to Step S12-4 to judge whether the one set of proper BP data stored in the RAM 66 at Step S12-1 represents the second latest date and time. If a positive judgment is made at Step S12-4, the control of the CPU 62 goes to Step S12-5 to store, in the late BP data memory area 80, the set of proper BP data indicative of the values SAP, DAP, MAP, PR together with the data indicative of the date and time of measurement of those values.

If a negative judgment is made at Step S12-4, Step S12-6 is implemented to judge whether the systolic BP value SAP represented by the one set of proper BP data stored in the RAM 66 at Step S12-1 is the highest of the respective values SAP represented by the sets of proper BP data stored in the proper BP data memory area 76. If a positive decision is made at Step S12-6, the control goes to Step S12-7 to store the set of proper BP data indicative of the values SAP, DAP, MAP, PR in the highest-SAP BP data memory area 82, together with the data indicative of the date and time of measurement of those values.

If a negative judgment is made at Step S12-6, the control of the CPU 62 goes to Step S12-8 to judge whether the systolic BP value SAP represented by the one set of proper BP data stored in the RAM 66 at Step S12-1 is the lowest. If a positive judgment is made at Step S12-8, Step S12-9 is implemented to store the set of proper BP data indicative of the values SAP, DAP, MAP, PR in the lowest-SAP BP data memory area 84, together with the data indicative of the date and time of measurement of those values.

If a negative judgment is made at Step S12-8, the control of the CPU 62 goes back to Step S12-1 to transfer the next set of proper BP data stored in the proper BP data memory area 76, to the RAM 66, and effects the following steps with respect to the next set of proper BP data stored in the RAM 66. Step S12-3, S12-5, S12-7, or S12-9 is followed by Step S12-10 to judge whether an appropriate set of proper BP data has been stored in each of the respective memory areas 78, 80, 82, 84. If a negative judgment is made at Step S12-10, the control of the CPU 62 goes back to Step S12-1 and the following steps. On the other hand, if a positive judgment is made at Step S12-10, the control goes to Step S12-11.

Figure 6:
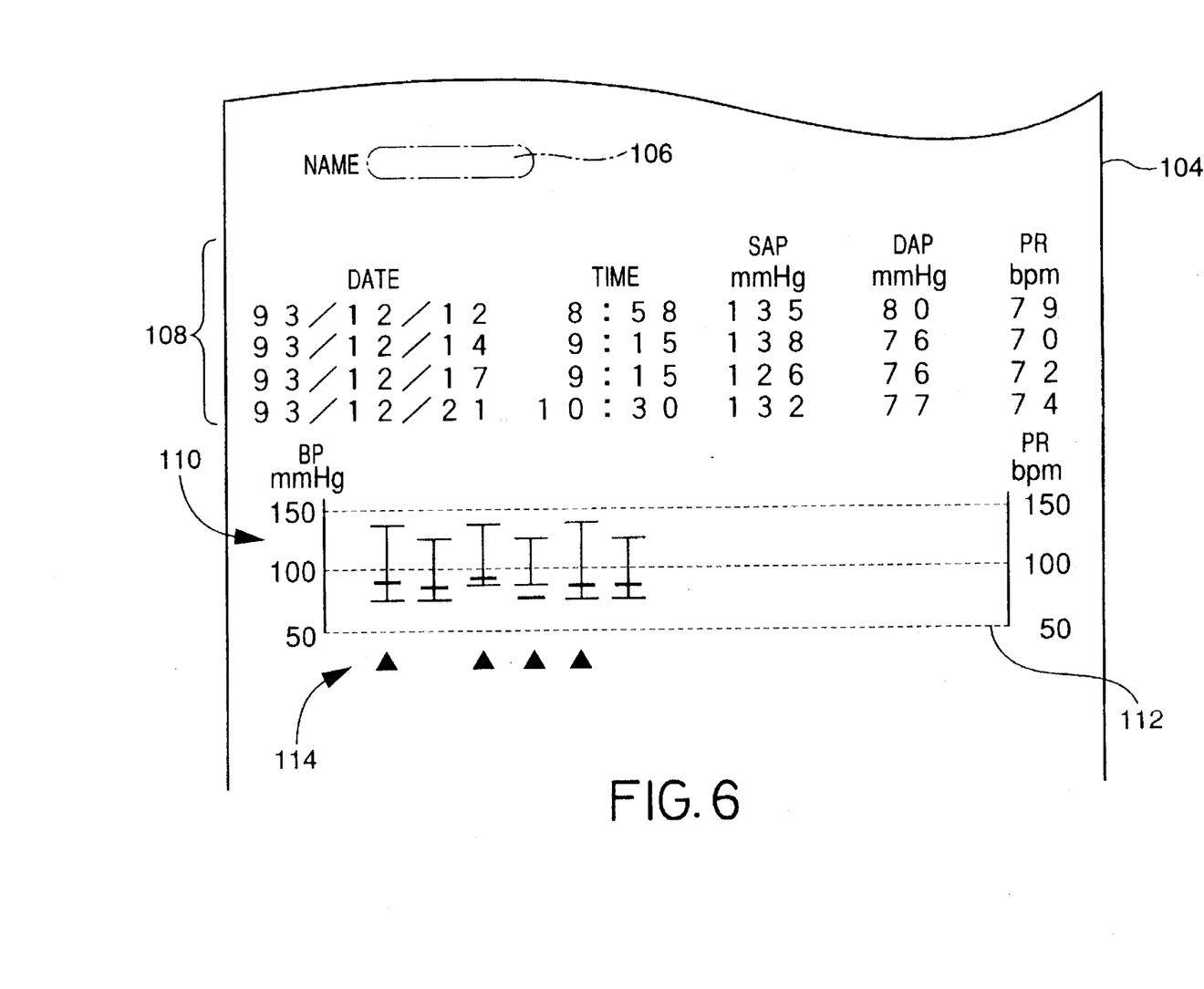
FIG. 6 is a view showing a printed sheet which is output from the apparatus of FIG. 1 as a result of operation thereof according to the flow chart of FIG. 3.

At Step S12-11, the CPU 62 commands the printer 28 to output or record, on a recording sheet 104, the BP data stored in the BP-data storing device 72, as shown in FIG. 6. More specifically described, in an upper, left-hand portion of the sheet 104, the printer 28 records a name 106 of the person identified by the ID data or magnetic card 88. The name 106 of the person is represented by the registered ID data identifying the person. Bellow the name 106, the printer 28 records (a) a data list 108 showing the date and time of measurement and the measured BP and pulse-rate values represented by each of the four sets of BP and pulse-rate data respectively stored in the early BP data memory area 78, late BP data memory area 80, highest-SAP BP data memory area 82, and lowest-SAP BP data memory area 84; and (b) a graphic representation 110 of all the sets of proper BP data accumulatively stored in the proper BP data memory area 76. The graphic representation 110 shows, along a common axis of abscissa 112 indicative of time, a series of vertical bars each of which has a top and a bottom thin horizontal segment which represent a systolic and a diastolic BP value SAP, DAP, respectively, and has a thick horizontal segment which represents a pulse-rate value PR, in the order of measurement. The bars are plotted at a regular interval of distance along the time axis 112. A symbol, ▲ 114, is recorded in association with each of the four bars, shown in the graphic representation 110, which respectively correspond to the four sets of proper BP data listed in the data list 108. Step S12 is followed by Step S13 of the main routine of FIG. 3 to eject the magnetic card 88 from the card reader 86.

As is apparent from the foregoing description, in the present embodiment, if a plurality of sets of temporary BP data are found in the temporary BP data memory area 74 at Step S11-2 of the subroutine of FIG. 4, the CPU 62 selects, at Step S11-4, one of the stored sets of temporary BP data which represents the lowest systolic BP value SAP of the respective systolic BP values SAP represented by all the stored sets of temporary BP data, and stores the selected set of temporary BP data as a set of proper BP data, together with data indicative of the date and time when the five minutes have passed after the first BP measurement is started, in the proper BP data memory area 76. Thus, in the case where the second or more BP measurements are effected for obtaining the second or more sets of BP data and thereby increasing the accuracy of BP measurements, only the most appropriate set of BP data is stored as a set of proper BP data in the proper BP data memory area 76. In this way, the memory capacity of the BP-data storing device 72 is utilized with efficiency. Furthermore, since unnecessary BP or pulse-rate values are not recorded in the graphic representation 110, the person can appropriately understand the time-wise change of his or her BP and/or pulse-rate values from the representation 110.

In the present embodiment, the time duration measured by the timer at Step S10 is predetermined at the five minutes. Since each BP measurement effected at Step S6 needs about one minute, at least three BP measurements can be carried out within the predetermined duration. Since, usually, at least one of the three BP measurements can provide accurate BP values of the living person, the predetermined duration is appropriate for almost all cases.

While the present invention has been described in its preferred embodiment, the present invention may otherwise be embodied.

For instance, in the illustrated embodiment, Step S12 of the main routine of FIG. 3, i.e., the displaying and outputting subroutine of FIG. 5 may be omitted. In the latter case, all the sets of proper BP data stored in the proper BP data memory area 76 may be utilized to record the data list 108 on the recording sheet 104.

In the illustrated embodiment, the CPU 62 determines the BP values of the living person according to the known oscillometric BP measuring method, in the BP measuring subroutine of Step S6 of FIG. 3. However, the BP measuring apparatus 10 may be modified to measure BP values according to a known Korotkoff-sound BP measuring method in which one or more BP values are determined based on detected Korotkoff sounds. In the latter case, the BP measuring apparatus 10 needs a microphone which detects Korotkoff sounds which are produced from arteries of a body portion (e.g., upper arm 14) of a living person while the pressure of the cuff 18 pressing the upper arm 14 is changed, i.e., gradually decreased or increased.

In the illustrated embodiment, the sets of proper BP data are accumulatively stored in the BP-data storing device 72. However, the sets of proper BP data may accumulatively be stored on the magnetic card 88, that is, another proper BP data memory area may be provided on the magnetic card 88. In the latter case, the various memory areas 74-84 may be provided in the RAM 66, and each set of proper BP data may be transferred from the proper BP data memory area 76 of the RAM 66 to that provided on the magnetic card 88, before the card 88 is ejected from the card reader 86. In this case, the BP-data storing device 72 may be replaced by the RAM 66.

It is to be understood that the present invention may be embodied with other changes, modifications, and improvements which may occur to those skilled in the art without departing from the spirit and scope of the invention defined in the appended claims.

What is claimed is:

1. An apparatus for measuring a blood pressure value of a living subject, comprising:

a blood pressure measuring device which measures, in each of a plurality of measuring operations, at least one actual blood pressure value of the subject including a systolic blood pressure value of the subject;

a first storing means for storing a set of provisional blood pressure data which represents at least one actual blood pressure value measured by said blood pressure measuring device in each of a plurality of measuring operations within a predetermined time duration, thereby storing a plurality of sets of provisional blood pressure data corresponding to said plurality of measuring operations within said time duration; and a second storing means for selecting one of said sets of provisional blood pressure data such that the selected one set of provisional blood pressure data represents at least one actual blood pressure value including a lowest systolic blood pressure value of the respective systolic blood pressure values represented by the sets of provisional blood pressure data, and storing said selected one set of provisional blood pressure data as a set of proper blood pressure data representing at least one proper blood pressure value obtained within said time duration.

2. An apparatus according to claim 1, further comprising a timer which measures said predetermined time duration.

3. An apparatus according to claim 2, further comprising a card reader which reads identification data recorded on a data card which is inserted in said card reader by the subject, wherein said timer starts to measure said predetermined time duration when said blood pressure measuring device starts an initial blood pressure measurement after said card reader reads the identification data from the data card.

4. An apparatus according to claim 1, further comprising a card reader which reads identification data recorded on a data card which is inserted in said card reader by the subject.

5. An apparatus according to claim 4, wherein said second storing means comprises means for storing said set of proper blood pressure data on the data card being inserted in said card reader.

6. An apparatus according to claim 4, further comprising:

a registering device which registers identification data identical with the identification data recorded on the data card; and judging means for judging whether the identification data read by said card reader from the data card inserted by the subject are identical with the identification data registered by the registering device.

7. An apparatus according to claim 6, wherein said second storing means comprises means for accumulatively storing a plurality of said sets of proper blood pressure data in association with the registered identification data.

8. An apparatus according to claim 1, wherein said blood pressure measuring device comprises means for measuring, in said each measuring operation, at least said systolic blood pressure value and a diastolic blood pressure value of the subject.

9. An apparatus according to claim 1, further comprising judging means for judging whether the first storing means has stored a single set of provisional blood pressure data, wherein said second storing means comprises means for storing, when said judging means makes a positive judgment, said single set of provisional blood pressure data as said set of proper blood pressure data.

10. An apparatus according to claim 1, further comprising an output device which outputs a graphic representation indicating a time-wise change of the sets of proper blood pressure data accumulatively stored by said second storing means.

11. An apparatus according to claim 1, wherein said blood pressure measuring device comprises an inflatable cuff which is adapted to be wound around a body portion of the subject.

12. An apparatus according to claim 1, wherein said second storing means comprises means for accumulatively storing a plurality of said sets of proper blood pressure data.

13. An apparatus according to claim 12, further comprising means for selecting, from the sets of proper blood pressure data stored by said second storing means an oldest set of proper blood pressure data which is stored by the second storing means prior to any other set of proper blood pressure data.

14. An apparatus according to claim 12, further comprising means for selecting, from the sets of proper blood pressure data stored by said second storing means, a second latest set of proper blood pressure data which is stored by the second storing means prior to the last stored set of proper blood pressure data.

15. An apparatus according to claim 12, further comprising means for selecting, from the sets of proper blood pressure data stored by said second storing means, a set of proper blood pressure data representing at least one proper blood pressure value including a highest systolic blood pressure value of the respective proper systolic blood pressure values represented by the sets of proper blood pressure data.

16. An apparatus according to claim 12, further comprising means for selecting, from the sets of proper blood pressure data stored by said second storing means, a set of proper blood pressure data representing at least one proper blood pressure value including a lowest systolic blood pressure value of the respective proper systolic blood pressure values represented by the sets of proper blood pressure data.

17. An apparatus according to claim 1, wherein said second storing means comprises means for storing said set of proper blood pressure data together with data representing a time when the set of proper blood pressure data is obtained.

18. An apparatus according to claim 1, further comprising a pulse-rate measuring device which measures a pulse-rate value of the subject, and wherein said second storing means stores said set of proper blood pressure data together with data representing the pulse-rate value measured when the proper blood pressure value represented by the set of proper blood pressure data is measured by said blood pressure measuring device.

* * * * *